US008679456B2

(12) United States Patent
Gadian

(10) Patent No.: US 8,679,456 B2
(45) Date of Patent: Mar. 25, 2014

(54) METHOD OF HYPERPOLARISING A MAGNETIC RESONANCE AGENT

(75) Inventor: David Geoffrey Gadian, Royston (GB)

(73) Assignee: David Geoffrey Gadian, Royston, Hertfordshire (GB)

( * ) Notice: Subject to any disclaimer, the term of this patent is extended or adjusted under 35 U.S.C. 154(b) by 534 days.

(21) Appl. No.: 12/667,352

(22) PCT Filed: Jul. 7, 2008

(86) PCT No.: PCT/GB2008/002323
§ 371 (c)(1),
(2), (4) Date: Dec. 30, 2009

(87) PCT Pub. No.: WO2009/004357
PCT Pub. Date: Jan. 8, 2009

(65) Prior Publication Data
US 2010/0191097 A1    Jul. 29, 2010

(30) Foreign Application Priority Data

Jul. 5, 2007 (GB) .................................. 0713074.3

(51) Int. Cl.
*A61B 5/055* (2006.01)
*A61K 49/00* (2006.01)
(52) U.S. Cl.
USPC ........................................... 424/9.1; 424/9.3
(58) Field of Classification Search
USPC ........................................................ 424/9.3
See application file for complete search history.

(56) References Cited

U.S. PATENT DOCUMENTS

| | | | |
|---|---|---|---|
| 6,125,654 A | 10/2000 | Honig | |
| 2002/0058869 A1 | 5/2002 | Axelsson et al. | |
| 2005/0232864 A1 | 10/2005 | Clark et al. | |
| 2007/0025918 A1 | 2/2007 | Hurd | |

FOREIGN PATENT DOCUMENTS

| | | | |
|---|---|---|---|
| WO | WO 98/58272 | | 12/1998 |
| WO | WO 9935508 A1 * | | 7/1999 |
| WO | WO 2005/004903 A1 | | 1/2005 |
| WO | WO 2006/054903 | | 5/2006 |
| WO | WO 2007/064226 | | 12/2006 |
| WO | WO 2007/064226 | | 6/2007 |
| WO | WO 2007064226 A2 * | | 6/2007 |
| WO | WO 2008/020764 A1 | | 2/2008 |

OTHER PUBLICATIONS

Bertini et al., *Electron-Nucleus Interactions and Their Biophysical Consequences*, Department of Chemistry, University Florence, Via G. Capponi, 7, 50121 Florence, Italy; and Department of Soil Science and Plant Nutrition, University of Florence, P.le delle Cascine 7.50144 Florence, Italy.
Golman et al., 13C imaging-a new diagnostic platform, European Radiology (2006), 16: pp. 57-67.
Kuhna et al., "Unexpextedly rapid 19F spin-lattice relaxation in CaF2 below 1 K," *Physical Review B* (1987) 35 (10): 4591-4593.
Waugh et al., "Mechanism of nuclear spin-lattice relaxation in insulators at very low temperatures," *Physical Review B* (1988) 37 (8): 4337-4339.
Golman et al., "Real-time metabolic imaging," *PNAS* (2006) 103 (30): 11270-11275.
Golman et al., "Molecular imaging with endogenous substances," *PNAS* (2007) 100 (18): 10435-10439.
Golman et al., "Metabolic imaging and other applications of hyperpolarizaed 13C1," *Acad. Radiol.* (2006) 13: 932-942.
Krjukov et al., "Brute force polarization of 129Xe," *Journal of Low Temperature Physics* (2005) 140 (5/6): 397-408.
Månsson et al, "13C imaging—a new diagnostic platform," *Eur. Radiol.* (2006) 16: 57-67. XP019336187.
Frank et al., "Dynamic dysprosium-DTPA-BMA enhanced MRI of the occipital cortex: Functional imaging in visually impaired monkeys by PET and MRI," Scientific and Exhibition. Proceedings, International Society for Magnetic Resonance in Medicine, US 188. XP008068747, 1990.
Bertini et al., *Electron-Nucleus Interactions and Their Biophysical Consequences, Department of Chemistry*, University of Florence, Via G. Capponi, 7, 50121 Florence, Italy; and *Department of Soil Science and Plant Nutrition*, University of Florence, P.le delle Cascine 7, 50144 Florence, Italy, 1998.
Bertini et al., "Electron-Nucleus Interactions and Their Biophysical Consequences", *Biophysics Textbook Online*. (Admitted Prior Art).
Bertini, Ivano, and Claudio Luchinat. "Electron-nucleus interactions and their biophysical consequences." Nuclear Magnetic Resonance. D. Gorenstein, Biophysical Society (1998).

* cited by examiner

*Primary Examiner* — Michael G Hartley
*Assistant Examiner* — Melissa Perreira
(74) *Attorney, Agent, or Firm* — Merchant & Gould P.C.

(57) ABSTRACT

A method of hyperpolarising a magnetic resonance (MR) agent is suitable for use in magnetic resonance imaging (MRI) or magnetic resonance spectroscopy (MRS). The method includes providing a solution comprising the MR agent suitable for use in MRI or MRS and at least one relaxation agent, the relaxation agent being a paramagnetic metal ion having an electron spin relaxation time of less than $1 \times 10^{-10}$ seconds at 20° C. The method further includes exposing the solution to a temperature of less than 5 K and a magnetic field of at least 1 T. The relaxation agent may, for example, be dysprosium.

13 Claims, No Drawings

METHOD OF HYPERPOLARISING A MAGNETIC RESONANCE AGENT

This application is a National Stage Application of PCT/GB2008/002323, filed Jul. 7, 2008, which claims benefit of Ser. No. 0713074.3, filed Jul. 5, 2007 in the United Kingdom and which applications are incorporated herein by reference. To the extent appropriate, a claim of priority is made to each of the above disclosed applications.

FIELD

This invention relates to a method of hyperpolarising a magnetic resonance agent suitable for use in Magnetic Resonance Imaging (MRI) or Magnetic Resonance Spectroscopy (MRS). The invention further relates to an improved method of MRI or MRS which includes the step of first preparing a hyperpolarised magnetic resonance (MR) agent.

BACKGROUND

Magnetic resonance imaging and spectroscopy are extensively used as diagnostic and research tools. Their use is widespread, in part because the methods are non-invasive and in human studies do not necessitate the exposure of the patient to potentially harmful radiation such as X-rays.

Magnetic resonance spectroscopy is widely used as an analytical tool for the investigation of molecular structure, dynamics, and metabolism, both in vitro and in vivo. Conventional MRI is based largely on the detection of signals from water, and from fats also, and has widespread applications in biomedical research and diagnostic radiology. While these techniques are very powerful, they would be even more powerful if fuller use could be made of the potential nuclear magnetism of the compounds being detected.

Magnetic resonance signal strength is partly dependent on the population difference between the nuclear spin states of the imaging nuclei, i.e. the difference between the populations of nuclear magnets aligned with and against an applied magnetic field. This difference is governed by the Boltzmann distribution.

Under thermal equilibrium conditions (for example at room or body temperature), the nuclear magnets aligned against the field have slightly higher energy than those aligned with it, and will as a result have a slightly smaller population. Because the population difference between the two states is very small, the nuclear magnetism is said to be weakly polarised (typically of the order of 0.01-0.001%).

In the case of proton MR, the weak level of polarisation has the effect that only a tiny proportion (typically of the order of 1 in 10,000-100,000) of the protons (for example in water) are detected, and the proportions are even smaller for other nuclei such as $^{13}C$, $^{15}N$, and $^{31}P$. There is therefore considerable interest in increasing this polarisation in order to enhance the overall sensitivity of the technique.

One approach is to increase the field strength, but there are constraints on providing ever more powerful magnets as well as potential ill effects for human studies. An alternative approach is to create an artificial, non-equilibrium distribution of the spin states of the nuclei; this may be described as the 'hyperpolarised' state.

Various hyperpolarisation methods applicable to $^{13}C$ nuclei are reviewed in Golman et al. (Eur. Radiol. 16, 57-67, 2006). One such method is the so-called 'brute force' approach wherein a sample is subjected to a very strong magnetic field at very low temperature. However, Golman concludes that for $^{13}C$ applications, this would require impractically low temperatures to be useful.

An analogous approach was taken by Honig in U.S. Pat. No. 6,125,654. The patent discloses a method of producing bulk hyperpolarised $^{129}Xe$ using a 'brute force' approach, wherein the $^{129}Xe$ is exposed to low temperature (e.g. 5-10 mK) and a high magnetic field (~10 T) to increase the polarisation level. However, the time required to reach a useful polarisation level (characterised by the spin-lattice relaxation time $T_1$) is inherently extremely long at low temperatures and high magnetic fields for spin ½ nuclei and thus in order to make the relaxation time practicable, Honig discloses the use of various 'relaxation switches'.

According to Honig, the first requirement of a relaxation switch is that it must provide for a decrease in the relaxation time $T_1$. The second requirement is that the relaxation switch must be removable so that when the xenon is removed from the low temperature and high field environment, the high polarisation level is not lost. Examples of suitable relaxation switches disclosed by Honig include: paramagnetic oxygen molecules, dispersed magnetized small particles encapsulated in polymers, stable free radicals, photosensitive molecules such as HI and HBr, o-$H_2$ and HD, impurities induced via irradiation and fixed magnetic wires.

A different approach was taken in Axelsson et al. (US 2002/0058869) where the spin refrigeration technique was employed. This technique involves doping the material to be polarised with paramagnetic ions and then placing the mixture in a strong magnetic field at low temperature and repeatedly or continuously re-orienting the material relative to the magnetic field. The technique disclosed in Axelsson requires that the material to be polarised is present in the solid state and preferably in the form of a single crystal. It is also taught that it is desirable that as great a proportion of the paramagnetic ions as possible should be separated from the MR imaging agent after hyperpolarisation, in order to improve physiological tolerability and to lengthen $T_1$, i.e. to prevent the rapid loss of hyperpolarisation once the spin refrigeration process has been completed.

A further method is the dynamic nuclear polarisation (DNP) method, see Golman et al. (Eur. Radiol. 16, 57-67, 2006). Under moderately low temperature and magnetic field conditions (e.g. 1 K and 3 T) the $^{13}C$ nuclear polarisation is below 0.1%, whereas the electrons are polarised to >90%. The DNP method relies on the transfer of the high polarisation of electron spins to coupled nuclear spins. This is achieved via microwave irradiation near the electron resonance frequency. The transfer is facilitated by doping the material to be hyperpolarised with a substance containing unpaired electrons. Most paramagnetic substances may be used as DNP agents (see WO 98/58272) e.g. transition metal ions and organic free radicals such as nitroxide radicals and trityl radicals. DNP can result in an increase in the level of nuclear polarisation in an imaging agent to 20-40% or more. However, the paramagnetic agents may be toxic and may require removal before injection of the hyperpolarised material into the body.

Herein, and elsewhere in the art, the term 'hyperpolarisation' is used to mean having a greater degree of polarisation than at equilibrium under typical magnetic resonance operating conditions (for example at room temperature and in a magnetic field of up to ~20 T). Thus a sample is also described as hyperpolarised when it is at a low temperature and in a high magnetic field so long as the degree of polarisation is higher than it would be at equilibrium at room temperature and in a magnetic field of up to ~20 T, even though the polarisation of the sample may in fact be at thermodynamic equilibrium under the applied high magnetic field and low temperature conditions.

While the methods described above go some way towards providing effective hyperpolarisation of agents for MRI and MRS, there remains a need for further, more effective methods of hyperpolarisation.

SUMMARY OF THE INVENTION

The invention provides a method of hyperpolarising a magnetic resonance (MR) agent suitable for use in magnetic resonance imaging (MRI) or magnetic resonance spectroscopy (MRS) comprising the steps of:
  a) providing a solution comprising the MR agent suitable for use in MRI or MRS and at least one relaxation agent, the relaxation agent being a paramagnetic metal ion having an electron spin relaxation time of less than $1 \times 10^{-10}$ seconds at 20° C.; and
  b) exposing the solution to a temperature of less than 5 K and a magnetic field of at least 1 T.

DETAILED DESCRIPTION OF THE INVENTION

It has now been found that a relaxation agent in accordance with the present invention causes a substantial decrease in the relaxation time T1 (the nuclear spin-lattice relaxation time) of the MR agent at low temperatures (i.e. less than 5 K), and has only a minimal effect on the relaxation time T1 of the MR agent at room temperature.

A method of MRI or MRS carried out using the method of the invention provides the advantage that the relaxation agent, i.e. the paramagnetic metal ion having an electron spin relaxation time of less than $1 \times 10^{-10}$ seconds at 20° C., enhances (i.e. accelerates) the rate of polarisation of the magnetic resonance (MR) agent during the hyperpolarisation step. Whereas without the relaxation agent, useful hyperpolarisation may take many years to achieve, with the relaxation agent present, useful levels of hyperpolarisation can be achieved in a much shorter time. For use, the MR agent is returned to higher (e.g. room) temperature and, significantly, the relaxation agent does not result in an unduly detrimental enhancement of the loss of hyperpolarisation when the MR agent is removed from the low temperature (less than 5 K) conditions. As used herein, the term magnetic resonance (MR) agent is used to refer to an agent that is suitable for use in MRI or MRS.

Under normal conditions, the nuclear magnets in a MR agent have a weak interaction with their surroundings. In order to increase the rate of hyperpolarisation, it is necessary to increase the interaction with their surroundings. Paramagnetic ions (which themselves are stronger magnets) can act as mediators and thus increase this interaction.

It is hypothesised that the relaxation agent, i.e. the at least one paramagnetic metal ion having an electron spin relaxation time of less than $1 \times 10^{-10}$ seconds at 20° C., is able to enhance the rate of hyperpolarisation without having an unduly detrimental acceleration of the loss of hyperpolarisation because of the particular varying nature of the electron spin relaxation time with temperature.

At room temperature, the 'flipping' of paramagnetic ions having an electron spin relaxation time of less than $1 \times 10^{-10}$ seconds at room temperature is too rapid to cause a strong $T_1$ interaction with the nuclei of the MR agent. The at least one paramagnetic ion is thus a relatively weak relaxation agent at room temperature. However, as the temperature is reduced, the electron spin relaxation time of the at least one paramagnetic ion with the above-defined characteristics will increase and therefore the rate of 'flipping' slows down and the interaction of the paramagnetic ions with the nuclei of the MR agent is increased. The at least one paramagnetic ion thus becomes a relatively strong relaxation agent at low temperatures. This can be characterised by a substantial reduction in the relaxation time T1 of the MR agent when in the presence of the relaxation agent. At extremely low temperatures (i.e. very close to absolute zero) when molecular motion approaches zero, the strength of the relaxation agent decreases again as its interactions with the MR agent become weaker.

It has been found that it is possible to select an ion with the appropriate electron spin relaxation characteristics (i.e. an electron spin relaxation time of less than $1 \times 10^{-10}$ seconds) so as to maximise its relaxation effects at low temperature relative to those at ambient (room) temperature.

In a preferred embodiment of the invention, the relaxation agent is a lanthanide ion. For example the relaxation agent may be a cerium, praseodymium, neodymium, promethium, samarium, europium, terbium, dysprosium, holmium, erbium, thulium or an ytterbium ion.

In a particularly preferred embodiment, those paramagnetic lanthanide ions having particularly short electron spin relaxation times, e.g. less than $1 \times 10^{-11}$ seconds, more preferably less than $1 \times 10^{-12}$ seconds or still more preferably less than $1 \times 10^{-13}$ seconds are used in the method of the invention. Particularly preferred lanthanide ions are selected from the group consisting of praseodymium, samarium, europium, dysprosium, erbium and holmium.

In a preferred embodiment, it is possible to select a particular concentration of the relaxation agent such that it has a significant hyperpolarising effect on a time scale of weeks or months or years (the time-scale of the intrinsic rate of hyperpolarisation at very low temperatures) whilst having an insignificant effect on the loss of hyperpolarisation over a time scale of seconds or minutes (the time scale of loss of hyperpolarisation in solution at room temperature). Such a concentration may lie in the range 0.1 µM to 1 M, preferably 1 µM to 100 mM, yet more preferably 10 µM to 1 mM, for example 0.1 mM.

The relaxation agent may be a single paramagnetic ion species or it may be a combination of at least two paramagnetic ion species.

The relaxation agent is preferably chelated. Chelation improves the solubility of the relaxation agent and reduces the toxicity of the solution comprising the hyperpolarised MR agent and the relaxation agent. Chelation thus allows for the mixture of the hyperpolarised MR agent and the relaxation agent to be introduced into a patient without the need to first separate the hyperpolarised MR agent from the relaxation agent. This provides the advantage that the method of carrying out the MRI/MRS procedure is simplified (i.e. a separation is step is not required) and further the time between the hyperpolarisation step and the actual MRI/MRS procedure is reduced, thus meaning that losses in hyperpolarisation are minimised. However, in an alternative embodiment, the relaxation agent may be separated from the hyperpolarised MR agent before introduction of the agent into a patient.

Any chelation agent known to a person skilled in the art which results in an improvement of the solubility of the relaxation agent and/or a reduction in the toxicity of the solution may be used in the method of the present invention. Examples of possible chelation agents include diethylenetriamine pentaacetic acid (DTPA), tetraazacyclododecanetetraacetic acid (DOTA), 10-(2-hydroxy-propy1)-1,4,7,10-tetraazacyclododecane-1,4,7-triacetic acid (HP-DO3A), and diethylenetriamine pentaacetic acid bismethylamide(DTPA- BMA). A particularly preferred chelation agent may be diethylenetriamine pentaacetate (DTPA). The precise choice of chelation agent depends on the properties required and the metal being used.

During the hyperpolarisation step of the method of the invention the solution of the MR agent and the relaxation agent are exposed to low temperature, e.g. lower than 5 K, preferably lower than 4.2 K, more preferably lower than 2.5 K, yet more preferably lower than 1.6 K, still more preferably lower than 1 K, even more preferably lower than 0.1 K, most preferably lower than or equal to 0.01 K.

Such temperatures may be achieved by any suitable method such as immersion in a liquid helium bath or via use of a cryogenic device such as a dilution refrigerator. The principle of a dilution refrigerator will be familiar to the person skilled in the art, but is briefly described here. The technique relies on a mixture of the two isotopes of helium $^3$He and $^4$He which, when cooled to a temperature below 700 mK, will undergo a spontaneous phase separation to form a $^3$He-rich phase and a $^3$He-poor phase. Energy is needed to transport $^3$He atoms from the rich phase into the poor phase and if atoms are continuously caused to cross the boundary from the rich phase to the poor phase, the mixture will be cooled.

One type of dilution refrigerator is known as a continuous-cycle dilution refrigerator in which the $^3$He atoms are recycled to start the process again once they have passed into the $^3$He-poor phase. Using such a system, it is possible to achieve temperatures lower than 0.002 K. An example of a dilution refrigerator that may be used in a method of the present invention is a Kelvinox 400 from Oxford Instruments, Abingdon, Oxfordshire, U.K.

During the hyperpolarisation step of the method of the invention the solution of the MR agent and the relaxation agent are also exposed to a high magnetic field, e.g. at least 1 T, preferably at least 3 T, more preferably at least 3.35 T, still more preferably at least 5 T, yet more preferably at least 7 T, even more preferably at least 10 T and most preferably at least 15 T.

High strength magnetic fields may be produced by any method known to the person skilled in the art, for example by use of superconducting magnets. An example of a suitable superconducting magnet is the ActiveShield 400 (9.4 T) from Oxford Instruments, Abingdon, Oxfordshire, U.K.

The level of polarisation produced in the MR agent is for example in excess of 0.1%, preferably in excess of 1%, more preferably in excess of 10%, yet more preferably in excess of 25%, still more preferably in excess of 50% and most preferably in excess of 75%. Such high levels of polarisation provide the advantage that for a particular magnetic field strength, more of the nuclei will be 'visible' and thus the signal to noise ratio value produced during a MRI or MRS procedure in an in vitro or an in vivo experiment will be higher. Consequently more detailed information can be provided by the MRI/MRS procedure. Among the many advantages, there would be scope for detecting much smaller quantities of the MR agent, and there may be less need to utilise very high field magnets.

The solution comprising the MR agent and the relaxation agent of the invention may be exposed to a temperature of less than 5 K and a magnetic field of at least 1 T for any period of time which results in a significant increase in the level of polarisation, for example to a level of polarisation in excess of 0.1%, preferably in excess of 1%, more preferably in excess of 10%, yet more preferably in excess of 25%, still more preferably in excess of 50% and most preferably in excess of 75%. Advantageously, the solution comprising the MR agent and the relaxation agent of the invention is exposed to a temperature of less than 5 K and a magnetic field of at least 1 T for less than 6 months, preferably for less than 3 months, more preferably for less than 1 month, yet more preferably for less than 7 days. Depending on the exact conditions used to achieve hyperpolarisation of the MR agent, in one embodiment the solution comprising the MR agent and the relaxation agent of the invention may be exposed to a temperature of less than 5 K and a magnetic field of at least 1 T for at least one hour. In another embodiment, the solution comprising the MR agent and the relaxation agent of the invention may be exposed to a temperature of less than 5 K and a magnetic field of at least 1 T for at least six hours, for example at least one day.

During the hyperpolarisation step of the method of the invention the solution comprising the MR agent and the relaxation agent is exposed to a temperature of less than 5 K and a magnetic field of at least 1 T. It is hypothesised that the enhancement to the rate of polarisation is achieved by interaction with the paramagnetic metal ion having an electron spin relaxation time of less than $1\times10^{-10}$ seconds at 20° C. In one embodiment, the solution is not simultaneously irradiated with microwave irradiation. In another embodiment, the solution is not repeatedly or continuously re-orientated relative to the magnetic field. In yet another embodiment, the solution is not irradiated with circularly polarised light.

The hyperpolarised MR agent remains hyperpolarised for a sufficiently long period, once removed from the low temperature conditions, to permit the downstream procedures to be performed within a comfortable time span.

In a particularly preferred embodiment, the MR agent remains mixed with the relaxation agent throughout the MRI or MRS procedure.

The invention also provides a method of hyperpolarising a magnetic resonance (MR) agent suitable for use in magnetic resonance imaging (MRI) or magnetic resonance spectroscopy (MRS) comprising the steps of:
a. providing a mixture comprising the MR agent suitable for use in MRI or MRS and at least one relaxation agent, the relaxation agent being a paramagnetic metal ion having an electron spin relaxation time of less than $1\times10^{-13}$ at 20° C.; and
b. exposing the mixture to a temperature of less than 5 K and a magnetic field of at least 1 T.

The features of the preferred embodiments described above may also be applied to this method of the invention.

The invention also provides a method of hyperpolarising a magnetic resonance (MR) agent suitable for use in magnetic resonance imaging (MRI) or magnetic resonance spectroscopy (MRS) comprising the steps of:
a. providing a solution containing the agent suitable for use in MRI or MRS and at least one relaxation agent, the relaxation agent being a paramagnetic metal ion;
b. exposing the solution to a temperature of less than 5 K and a magnetic field of at least 1 T.

The features of the preferred embodiments described above may also be applied to this method of the invention.

The invention further provides a method of magnetic resonance imaging (MRI) or magnetic resonance spectroscopy (MRS) wherein the imaging or spectroscopy procedure is carried out using a magnetic resonance (MR) agent suitable for use in MRI or MRS that has been hyperpolarised according to the method of the invention.

In another embodiment, the invention provides a kit comprising at least one relaxation agent, the relaxation agent being a paramagnetic metal ion having an electron spin relaxation time of less than $1\times10^{-10}$ seconds at 20° C. and instructions for its use in the methods of the invention.

In a further embodiment, the invention provides a kit comprising a magnetic resonance (MR) agent suitable for use in magnetic resonance imaging or magnetic resonance spectroscopy and at least one relaxation agent, the relaxation agent being a paramagnetic metal ion having an electron spin relaxation time of less than $1\times10^{-10}$ seconds at 20° C. and instructions for their use in the methods of the invention.

The methods of the present invention may be used to hyperpolarise any non zero nuclear spin nuclei. In a preferred embodiment the MR-visible nuclei of the MR agent exhibit a long $T_1$ relaxation time. An MR agent that has a long $T_1$ relaxation time is defined as having a $T_1$ value of at least 6 seconds in $D_2O$ at 37° C. and at a field of 7 T. Preferably the $T_1$ value is 8 seconds or more, more preferably 15 seconds or more, still more preferably 30 seconds or more, even yet more preferably 60 seconds or more and most preferably 100 seconds or more. Suitable nuclei with long $T_1$ relaxation times include $^{13}C$, $^{15}N$, $^{19}F$, $^3Li$, $^6Li$, $^{15}N$, $^{29}Si$ or $^{31}P$.

The methods of the present invention may be used to hyperpolarise any suitable MR agent. Where the MR-visible isotope of a particular atom of an MR agent is not the most naturally abundant isotope, the MR agent is preferably enriched with at least one MR-visible isotope such as $^{13}C$ or $^{15}N$. The MR agent may be enriched at one site or several sites. Enrichment may be achieved by any method known to the person skilled in the art, for instance by chemical synthesis or biological labelling. Preferably the enrichment level is at least 10%, more preferably at least 25%, still more preferably at least 75%, yet more preferably at least 90% and most preferably approaching 100%.

The MR agent may be a small molecule having a relatively low molecular weight (e.g. less than 500 D), or it may be a larger molecule for example a protein. In one embodiment of the invention, the MR agent may be used to probe specific tissues or biological processes in vivo. In a preferred embodiment, the at least one MR-visible atom of the MR agent is influenced by the environmental conditions in which the MR agent is placed. In a particularly preferred embodiment, the chemical shift or the coupling constant of the MR signal of the at least one MR-visible atom is influenced by changes in physiological parameters such as temperature, pH, ion concentration etc. Such an MR agent may thus be used to follow changes in physiological parameters in real time. The MR agent may be transformed during an MRI/MRS procedure into another molecule, which has a concomitant effect on the chemical shift or the coupling constant of the MR signal of the at least one MR-visible atom. Particularly preferred MR agents for the in vivo probing of tissues and biological processes are small molecules for example sugars, amino acids, peptides and other metabolites for example pyruvate, acetate, lactate, succinate, bicarbonate and choline, and ions such as lithium. Agents such as helium and xenon, which are gases at room temperature and atmospheric pressure, may be used as MR agents. Such substances may or may not be naturally present in the body. Alternatively, the MR agent used for in vivo probing may be a larger molecule for example a protein. In a further embodiment, the MR agents, both large and small, can themselves be the subject of in vitro MR analysis.

In one embodiment, the MR agent is preferably soluble in a solvent, more preferably an aqueous solvent. Particularly preferred solvents for the hyperpolarisation step include water, in particular physiologically tolerable aqueous solutions, for example saline, Ringer's solution, dextrose solution, dextrose and saline solution, lactated Ringer's solution and other similar solutions such as are described in Remington's Pharmaceutical Sciences, 15$^{th}$ ed., Easton: Mack Publishing Co., p 1405-1412 and 1461-1487 (1975) and the National Formulary XIV, 14$^{th}$ ed. Washington: America Pharmaceutical Association (1975). The solvent may contain further constituents such as stabilisers, antioxidants, osmolality adjusting agents and/or buffers. The solution comprising the MR agent and the relaxation agent is expected to become solid at the temperature of less than 5 K. In order to prevent crystallisation of the solution, the solution may comprise at least one glass former (also known as a glassing agent). Suitable glass formers are for example glycerol, propanediol or glycol. Some MR agents or relaxation agents may themselves be glass formers and it may not be necessary to add a further component to achieve the necessary level of glassing.

In the case of certain MR agents, the solution comprising the MR agent and the relaxation agent may be a solution of the relaxation agent in the MR agent.

The method of the invention typically includes the step of: removing the solution from the magnetic field of at least 1 T and the low temperature (i.e. less than 5 K) conditions.

The process of bringing the solution to room temperature and removing it from the strong magnetic field may be carried out in several steps. For example it may be advantageous to maintain the solution at low temperature whilst removing it from the magnetic field. Alternatively, it may be beneficial to maintain the exposure of the solution to the magnetic field whilst bringing the solution to room temperature. The process of bringing the solution to room temperature and removing it from the strong magnetic field may involve exposing the solution for a period of time to an intermediate temperature that is higher than the initial temperature and/or exposing the solution to a magnetic field of intermediate strength that is lower than the strength of the initial magnetic field.

The downstream MRI/MRS procedures using the hyperpolarised MR agent may be carried out in vivo, i.e. the MR agent is introduced into a body (for example a human or animal body) and then an imaging or spectroscopy procedure is carried out on the agent within the body. In an alternative embodiment, the hyperpolarised MR agent itself may be the subject of in vitro imaging or spectroscopy procedure.

In the embodiment of the invention in which the hyperpolarised MR agent is studied in vivo, the hyperpolarised MR agent may be brought rapidly to room or body temperature prior to administration to a subject. This may be achieved by any suitable method known to the person skilled in the art. For example, the hyperpolarised MR agent may be mixed with an appropriate amount of a solution that has been pre-warmed to an appropriate temperature ('the administration solution'). The appropriate volume and temperature of the administration solution that is necessary to bring the hyperpolarised MR agent to the appropriate temperature and final concentration may be readily determined by the skilled person. The administration solution may contain further constituents which are appropriate for parenteral administration such as stabilisers, antioxidants, osmolality adjusting agents and/or buffers.

The route by which the hyperpolarised MR agent is administered to a subject depends on the nature of the agent itself and the investigation to be carried out. The agent may be administered, for example, via intravenous, intra-arterial, intramuscular, subdermal or subcutaneous injection. Where the lungs are to be imaged, the agent may be administered by a spray, e.g. an aerosol spray. The agent may also be administered non-parentally, e.g. via the gastrointestinal tract.

For use in in vivo experiments, the hyperpolarised MR agent may be administered at a concentration that is appropriate for the investigation being carried out, e.g. in vivo imaging. The appropriate concentration, to be determined by the skilled person, depends on a variety of factors such as toxicity of the agent and the administration route. Typically, the MR agent will be diluted between the hyperpolarisation and administration. If the hyperpolarised MR agent itself is to be investigated in an in vitro experiment, it may be studied in the solid state at low temperature or it may be brought to room temperature, for example by dissolution or thawing in a pre-warmed solution as described above.

The actual MRI or MRS procedure to be carried out using the hyperpolarised MR agent may be carried out using the methods that are well-known to the person skilled in the art. Examples of such methods are given in Golman et al (Proc. Natl. Acad. Sci. USA 103:11270-11275, 2006) and references therein.

EXAMPLES

Example 1

Hyperpolarisation of $^{13}$C-Enriched Pyruvate

A vial containing 1 ml of a solution of 300 mM $^{13}$C-enriched pyruvate and 0.1 mM Dysprosium-DTPA in aqueous, buffer, adjusted to pH 7.4 is introduced into the cooling chamber of a Kelvinox 400 dilution refrigerator. The cooling chamber is surrounded by a superconducting solenoid (an ActiveShield 400 (9.4 T)) such that the vial is positioned centrally in the field of the solenoid.

The temperature of the cooling chamber is reduced to 0.01 K, whilst applying a magnetic field of 9.4 T. The cooling chamber is held under these conditions for a period of 1 month thus allowing the nuclear polarisation of the $^{13}$C nuclei to achieve thermal equilibrium. It is possible to measure the degree of polarisation by NMR.

Following hyperpolarisation, the vial is removed from the cooling chamber and moved to an intermediate storage chamber held at a temperature of 4.2 K via immersion in a liquid helium bath and exposed to a moderate strength magnetic field of 1 T. Following storage in the intermediate storage chamber for a period of 2 days, it is possible to confirm by NMR that the hyperpolarisation of the $^{13}$C nuclei produced during the ultra low temperature stage is substantially preserved.

Example 2

Hyperpolarisation of $^{13}$C-Enriched Acetate

A vial containing 50 microlitres of an aqueous solution of 2 molar [1-13 C] sodium acetate, 12 mM Dys-DTPA and 50% glycerol was placed in a helium-cooled variable temperature insert positioned within the bore of a 3.35 T Oxford Instruments magnet. The temperature was reduced to 1.5K by pumping on the helium bath using a rotary vane pump. The presence of Dys-DTPA reduced the $^{13}$C T1 to approximately 40 minutes, compared with a T1 value of over 10 hours in the absence of Dys-DTPA.

An identical pair of solutions was prepared at 20-fold dilution relative to the concentrations of the solutions used above, so that the concentration of [1-13 C] sodium acetate was 100 mM and the concentration of Dys-DTPA was 0.6 mM. At a field strength of 11.7 T and temperature of 21° C., the presence of 0.6 mM Dys-DTPA reduced the $^{13}$C T1 value of [1-13 C] sodium acetate (which was approximately 40 seconds in the absence of Dys-DTPA) by less than 10%.

The presence of Dys-DTPA caused a marked decrease in the $^{13}$C T1 of [1-13 C] sodium acetate at low temperature and had only a minimal effect at high temperature. Dys-DTPA is thus a suitable relaxation agent for use in the methods of the invention.

The invention claimed is:

1. A method of hyperpolarising a magnetic resonance (MR) agent suitable for use in magnetic resonance imaging (MRI) or magnetic resonance spectroscopy (MRS) comprising the steps of:
   a. providing a solution comprising the MR agent suitable for use in MRI or MRS and at least one relaxation agent, the relaxation agent being a paramagnetic metal ion having an electron spin relaxation time of less than $1 \times 10^{-10}$ seconds at 20° C.; and
   b. exposing the solution to a temperature of less than 5 K and a magnetic field of at least 1 T;
   wherein the solution is not simultaneously irradiated with microwave irradiation; and
   wherein the solution is not repeatedly or continuously re-oriented relative to the magnetic field.

2. A method as claimed in claim 1, wherein the relaxation agent is a lanthanide ion.

3. A method as claimed in claim 2, wherein the lanthanide ion is selected from the group consisting of praseodymium, samarium, europium, dysprosium, erbium, and holmium ions.

4. A method as claimed in claim 1, wherein the relaxation agent is chelated.

5. A method as claimed in claim 4, wherein the chelating agent is Diethylenetriamine pentaacetate (DTPA).

6. A method as claimed in claim 1 wherein the solution is exposed to a temperature of less than 0.1 K.

7. A method as claimed in claim 1 wherein the solution is exposed to a magnetic field of at least 5 T.

8. A method as claimed in claim 1 wherein the hyperpolarisation level of the MR agent suitable for use in MRI or MRS is at least 10%.

9. A method of hyperpolarising a magnetic resonance (MR) agent suitable for use in magnetic resonance imaging (MRI) or magnetic resonance spectroscopy (MRS) comprising the steps of:
   a. providing a mixture comprising the MR agent suitable for use in MRI or MRS and at least one relaxation agent, the relaxation agent being a paramagnetic metal ion having an electron spin relaxation time of less than $1 \times 10^{-13}$ seconds at 20° C.; and
   b. exposing the, mixture to a temperature of less than 5 K and a magnetic field of at least 1 T;
   wherein the mixture is not simultaneously irradiated with microwave irradiation; and
   wherein the mixture is not repeatedly or continuously re-oriented relative to the magnetic field.

10. A method of hyperpolarising a magnetic resonance (MR) agent suitable for use in magnetic resonance imaging (MRI) or magnetic resonance spectroscopy (MRS) comprising the steps of:
   a. providing a solution comprising the MR agent suitable for use in MRI or MRS and at least one relaxation agent, the relaxation agent being a paramagnetic metal ion having an electron spin relaxation time of less than $1 \times 10^{-10}$ seconds at 20° C.; and
   b. exposing said MR agent and said relaxation agent to a temperature of less than 5 K and a magnetic field of at least 1 T;
   wherein said MR agent and said relaxation agent are not simultaneously irradiated with microwave irradiation; and wherein said MR agent and said relaxation agent are not repeatedly or continuously re-oriented relative to the magnetic field.

11. A method as claimed in claim 1, wherein the solution is not irradiated with circularly polarized light.

12. A method as claimed in claim 9, wherein the mixture is not irradiated with circularly polarized light.

13. A method as claimed in claim 10, wherein said MR agent and said relaxation agent are not irradiated with circularly polarized light.

* * * * *